United States Patent
Cunningham

(10) Patent No.: US 9,943,366 B2
(45) Date of Patent: *Apr. 17, 2018

(54) MICROWAVE SPACERS AND METHOD OF USE

(71) Applicant: COVIDIEN LP, Mansfield, MA (US)

(72) Inventor: Robert B. Cunningham, Longmont, CO (US)

(73) Assignee: Covidien LP, Mansfield, MA (US)

( * ) Notice: Subject to any disclaimer, the term of this patent is extended or adjusted under 35 U.S.C. 154(b) by 548 days.

This patent is subject to a terminal disclaimer.

(21) Appl. No.: 14/603,499

(22) Filed: Jan. 23, 2015

(65) Prior Publication Data

US 2015/0164585 A1 Jun. 18, 2015

Related U.S. Application Data

(63) Continuation of application No. 12/877,182, filed on Sep. 8, 2010, now Pat. No. 8,945,144.

(51) Int. Cl.
*A61B 18/04* (2006.01)
*A61B 18/18* (2006.01)
*A61B 17/34* (2006.01)

(52) U.S. Cl.
CPC ...... *A61B 18/1815* (2013.01); *A61B 17/3403* (2013.01); *A61B 2017/3407* (2013.01); *A61B 2017/3411* (2013.01); *A61B 2018/1861* (2013.01)

(58) Field of Classification Search
CPC ............ A61B 18/1815; A61B 17/3403; A61B 2017/3407; A61B 2017/3411; A61B 2018/1861
See application file for complete search history.

(56) References Cited

U.S. PATENT DOCUMENTS

| | | | |
|---|---|---|---|
| 3,631,363 | A | 12/1971 | Miller |
| D223,367 | S | 4/1972 | Kountz |
| D266,842 | S | 11/1982 | Villers et al. |
| 4,397,313 | A | 8/1983 | Vaguine |
| 4,462,412 | A | 7/1984 | Turner |

(Continued)

FOREIGN PATENT DOCUMENTS

| | | |
|---|---|---|
| DE | 390937 C | 3/1924 |
| DE | 1099658 B | 2/1961 |

(Continued)

OTHER PUBLICATIONS

Johnson, "Evaluation of the LigaSure.TM. Vessel Sealing System in Hemorrhoidectormy" American College of Surgeons (ACS) Clinic La Congress Poster (2000).

(Continued)

*Primary Examiner* — Lindsey G Wehrheim

(57) ABSTRACT

A microwave spacer for guiding and positioning microwave energy delivery devices during a surgical procedure includes a spacer including a body forming a plurality of device apertures defined therein. The plurality of device apertures includes at least two lumens and at least one arcuate slot. The lumens are configured to receive an energy delivery device therethrough. The arcuate slot includes a length, a width and a radius of curvature and is configured to receive an additional energy delivery device therethrough.

18 Claims, 14 Drawing Sheets

(56) References Cited

U.S. PATENT DOCUMENTS

| | | | |
|---|---|---|---|
| D278,306 S | 4/1985 | McIntosh | |
| 4,572,190 A | 2/1986 | Azam et al. | |
| 4,723,544 A | 2/1988 | Moore et al. | |
| 4,798,215 A | 1/1989 | Turner | |
| 5,097,844 A | 3/1992 | Turner | |
| D354,218 S | 1/1995 | Van De Peer | |
| 5,417,210 A | 5/1995 | Funda et al. | |
| 5,449,360 A | 9/1995 | Schreiber | |
| 5,623,931 A | 4/1997 | Wung et al. | |
| 5,626,607 A | 5/1997 | Malecki et al. | |
| 5,924,992 A | 7/1999 | Park et al. | |
| 6,031,375 A | 2/2000 | Atalar et al. | |
| D424,693 S | 5/2000 | Pruter | |
| 6,241,725 B1 | 6/2001 | Cosman | |
| 6,267,770 B1 | 7/2001 | Truwit | |
| 6,355,033 B1 | 3/2002 | Moorman et al. | |
| 6,375,606 B1 | 4/2002 | Garibaldi et al. | |
| 6,451,015 B1 | 9/2002 | Rittman, III et al. | |
| 6,564,806 B1 | 5/2003 | Fogarty et al. | |
| 6,603,994 B2 | 8/2003 | Wallace et al. | |
| 6,652,520 B2 | 11/2003 | Moorman et al. | |
| D487,039 S | 2/2004 | Webster et al. | |
| 6,725,080 B2 | 4/2004 | Melkent et al. | |
| 7,008,421 B2 | 3/2006 | Daniel et al. | |
| 7,197,363 B2 | 3/2007 | Prakash et al. | |
| 7,226,446 B1 | 6/2007 | Mody et al. | |
| 7,278,991 B2 | 10/2007 | Morris et al. | |
| 7,282,049 B2 | 10/2007 | Orszulak et al. | |
| D576,932 S | 9/2008 | Strehler | |
| 7,422,586 B2 | 9/2008 | Morris et al. | |
| 7,439,736 B2 | 10/2008 | Meaney et al. | |
| 7,452,331 B1 | 11/2008 | Pruter | |
| 7,467,015 B2 | 12/2008 | van der Weide | |
| D594,736 S | 6/2009 | Esjunin | |
| D594,737 S | 6/2009 | Kelly et al. | |
| 7,553,309 B2 | 6/2009 | Buysse et al. | |
| 7,565,207 B2 | 7/2009 | Turner et al. | |
| 7,625,371 B2 | 12/2009 | Morris et al. | |
| 7,642,451 B2 | 1/2010 | Bonn | |
| D613,412 S | 4/2010 | DeCarlo | |
| 7,697,972 B2 | 4/2010 | Verard et al. | |
| D673,685 S | 1/2013 | Cunningham | |
| 8,945,144 B2 * | 2/2015 | Cunningham | A61B 17/3403 606/129 |
| 2002/0022836 A1 | 2/2002 | Goble et al. | |
| 2003/0032951 A1 | 2/2003 | Rittman et al. | |
| 2004/0242992 A1 | 12/2004 | Hareyama | |
| 2004/0267256 A1 | 12/2004 | Garabedian et al. | |
| 2005/0149010 A1 | 7/2005 | Turovskiy et al. | |
| 2005/0149101 A1 | 7/2005 | Huschmand Nia | |
| 2006/0122581 A1 | 6/2006 | Ein-Gal | |
| 2006/0142757 A1 | 6/2006 | Daniel et al. | |
| 2007/0135821 A1 | 6/2007 | Shabaz | |
| 2007/0203480 A1 | 8/2007 | Mody et al. | |
| 2007/0233157 A1 | 10/2007 | Mark et al. | |
| 2008/0021448 A1 | 1/2008 | Orszulak et al. | |
| 2008/0183165 A1 | 7/2008 | Buysse et al. | |
| 2009/0076497 A1 | 3/2009 | Morris et al. | |
| 2009/0138005 A1 | 5/2009 | Prakash et al. | |
| 2009/0171203 A1 | 7/2009 | Avital et al. | |
| 2009/0187180 A1 | 7/2009 | Brannan | |
| 2009/0192510 A1 | 7/2009 | Bahney | |
| 2009/0198226 A1 | 8/2009 | Prakash et al. | |
| 2009/0198227 A1 | 8/2009 | Prakash | |
| 2009/0222002 A1 | 9/2009 | Bonn et al. | |
| 2009/0248005 A1 | 10/2009 | Rusin et al. | |
| 2009/0248006 A1 | 10/2009 | Paulus et al. | |
| 2009/0264877 A1 | 10/2009 | DeCarlo | |
| 2009/0264899 A1 | 10/2009 | Appenrodt et al. | |
| 2009/0295674 A1 | 12/2009 | Bonn | |
| 2009/0306652 A1 | 12/2009 | Buysse et al. | |
| 2009/0306659 A1 | 12/2009 | Buysse | |
| 2009/0326620 A1 | 12/2009 | Rossetto et al. | |
| 2010/0030206 A1 | 2/2010 | Brannan et al. | |
| 2010/0030208 A1 | 2/2010 | Manley | |
| 2010/0030210 A1 | 2/2010 | Paulus | |
| 2010/0036379 A1 | 2/2010 | Prakash et al. | |
| 2010/0045558 A1 | 2/2010 | Rossetto | |
| 2010/0045559 A1 | 2/2010 | Rossetto | |
| 2010/0049185 A1 | 2/2010 | Paulus | |
| 2010/0049193 A1 | 2/2010 | Huseman | |
| 2010/0053015 A1 | 3/2010 | Willyard | |
| 2010/0057070 A1 | 3/2010 | Behnke et al. | |
| 2010/0076422 A1 | 3/2010 | Podhajsky | |
| 2010/0082082 A1 | 4/2010 | Prakash et al. | |
| 2010/0087808 A1 | 4/2010 | Paulus | |
| 2010/0094272 A1 | 4/2010 | Rossetto et al. | |
| 2010/0094273 A1 | 4/2010 | Rossetto et al. | |
| 2010/0097284 A1 | 4/2010 | Brannan et al. | |
| 2010/0101825 A1 | 4/2010 | Bonn | |
| 2010/0217251 A1 | 8/2010 | Rossetto et al. | |
| 2010/0217252 A1 | 8/2010 | Rossetto et al. | |
| 2010/0228251 A1 | 9/2010 | Horlle | |
| 2010/0234839 A1 | 9/2010 | Smith et al. | |
| 2010/0256624 A1 | 10/2010 | Brannan et al. | |
| 2010/0262134 A1 | 10/2010 | Jensen et al. | |
| 2011/0034919 A1 | 2/2011 | DeCarlo | |
| 2011/0077636 A1 | 3/2011 | Brannan et al. | |
| 2012/0101487 A1 | 4/2012 | Cunningham et al. | |
| 2012/0265098 A1 | 10/2012 | McGhie | |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 481 685 A1 | 4/1992 |
| EP | 0 521 264 A2 | 1/1993 |
| EP | 0 556 705 A1 | 8/1993 |
| EP | 0 558 429 A1 | 9/1993 |
| EP | 0572131 A1 | 12/1993 |
| EP | 0541930 B1 | 3/1998 |
| EP | 0 836 868 A2 | 4/1998 |
| EP | 1 070 518 A2 | 1/2001 |
| EP | 1 159 926 A2 | 12/2001 |
| EP | 1278007 | 1/2003 |

(56) References Cited

FOREIGN PATENT DOCUMENTS

| | | |
|---|---|---|
| EP | 1 645 234 A1 | 4/2006 |
| EP | 1186274 | 4/2006 |
| EP | 1645235 A1 | 4/2006 |
| EP | 1 810 627 A1 | 7/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 166452 | 11/1964 |
| SU | 401367 A1 | 10/1973 |
| SU | 727201 A2 | 4/1980 |
| WO | 97/41924 A1 | 11/1997 |
| WO | 97/43971 A2 | 11/1997 |
| WO | 9904710 A1 | 2/1999 |
| WO | 00/48672 A1 | 8/2000 |
| WO | 00/51513 A1 | 9/2000 |
| WO | 01/01847 | 1/2001 |
| WO | 01/742452 A2 | 10/2001 |
| WO | 02/45790 A2 | 6/2002 |
| WO | 02/061880 A2 | 8/2002 |
| WO | 2004/112628 A1 | 12/2004 |
| WO | 2005/016119 A2 | 2/2005 |
| WO | 2005009528 A1 | 2/2005 |

OTHER PUBLICATIONS

Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
Mdtech product literature (Mar. 2000) I'D Wire: product description, 1 page.
Mdtech product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, OApr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
S Humphries Jr. et al., "FiniteElement Codes to Model Electrical Heating and Non.cndot.Llnear Thermal Transport in Biological Media", Proc. ASME HTD-355, 131 (1997).
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.

(56) References Cited

OTHER PUBLICATIONS

European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
U.S. Appl. No. 08/483,742, filed Jun. 7, 1995.
U.S. Appl. No. 08/136,098, filed Oct. 14, 1993.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/536,616, filed Aug. 6, 2009.
U.S. Appl. No. 12/877,182, filed Sep. 8, 2010.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw.cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.

(56) References Cited

OTHER PUBLICATIONS

Jarrett et al., "Use of the LigaSure.TM. Vessel Sealing System for Peri-Hilar Vessels in Laparoscopic Nephrectomy" Sales/Product Literature 2000.

* cited by examiner

MICROWAVE SPACERS AND METHOD OF USE

CROSS-REFERENCE TO RELATED APPLICATIONS

This application is a continuation application of U.S. patent application Ser. No. 12/877,182 filed on Sep. 8, 2010, the entire contents of which are incorporated by reference herein.

BACKGROUND

1. Technical Field

The present disclosure relates to apparatuses, systems and methods for providing energy to biological tissue and, more particularly, apparatuses, systems and methods for precise placement of microwave energy delivery devices during a surgical procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radiofrequency electrical current to a surgical site to cut, ablate, coagulate or seal tissue. In monopolar electrosurgery, a source or active electrode delivers radio-frequency energy from the electrosurgical generator at a predetermined frequency to the tissue and a return electrode carries the current back to the generator. In monopolar electrosurgery, the source electrode is typically part of the surgical instrument held by the surgeon and applied to the tissue to be treated and a patient return electrode is placed remotely from the active electrode to carry the current back to the generator. In bipolar electrosurgery, the active and return electrodes are placed in close proximity to each other, e.g., at the surgical site, and electrosurgical currents are passed therebetween. In microwave electrosurgery, the antenna of the microwave energy delivery device generates electromagnetic fields in the adjacent tissue without the generation of electrosurgical currents between an active electrode and a return electrode as discussed hereinabove.

Radio-frequency energy may be delivered to targeted tissue in an ablation procedure by electro surgical probes or by an electrosurgical antenna. In the case of tissue ablation using electrosurgical probes, electrode pairs are positioned in the surgical site to deliver high frequency electrosurgical currents between the pairs of active (+) and return (−) electrodes. An active (+) electrode and a return (−) electrode may be positioned in a spaced apart relationship on the shaft of an electrosurgical probe such that electrosurgical currents are passed along, or parallel to the shaft.

Alternatively, a first probe may function as an active (+) electrode and a second probe may function as a return (−) electrode. The first and second probes are positioned in a spaced apart relationship relative to each other such that electrosurgical currents are passed between the active (+) and return (−) electrodes resulting in the ablation of tissue positioned between the two probes. As such, the ablation region is defined by the spacing between the active (+) and return (−) electrodes and heating of tissue is typically confined therebetween. During ablation, current pathway's in tissue between the active (+) and return (−) electrode produce localized heating between the two probes.

Radio-frequency energy in a microwave frequency range may be delivered to a targeted tissue by a microwave energy delivery device with a microwave antenna on the distal tip. The antenna of the microwave energy delivery device, when provided with a microwave energy signal, generates electromagnetic fields in the adjacent tissue without the generation of electrosurgical currents between an active electrode and a return electrode as discussed hereinabove.

While the ablation region produced by ablation probes is defined by the current path between the electrodes, the ablation region (shape and area) produced by a microwave energy delivery device is defined by the type of antenna, the frequency of the microwave energy signal and the power level of the microwave energy signal. For example, an ablation region generated by a microwave energy delivery device may be symmetric about the tip and shaft of the microwave energy delivery device, directed to only one side of the shaft or if the antenna is unchoked, the ablation region may include a "tail" portion that extends proximally along the elongated shaft of the microwave energy delivery device.

Unlike radio-frequency probes, microwave energy delivery devices need not be configured to interact with each other. In fact, microwave energy delivery devices typically do not interact since any interaction would be due to the intermingling of the electromagnetic fields generated by the two devices (i.e., the two devices placed in close proximity may result in the overlapping of electromagnetic fields generated by each microwave energy delivery device). The overlapping electromagnetic fields may result in unpredictable results as the electromagnetic fields may cancel each other (resulting in no heating), the electromagnetic fields may combine (resulting in the generation of pockets of extremely high current densities) or any combination thereof. As such, controlling the interaction between microwave energy delivery devices becomes even more complicated when the surgical procedures requires the insertion of a plurality of microwave energy delivery devices.

The unpredictable nature of the overlapping electromagnetic fields can be overcome by precisely placing the microwave energy delivery devices in a target tissue.

SUMMARY

The present disclosure describes apparatuses, systems and methods for precise placement of energy delivery devices in a surgical procedure. In one embodiment, the energy delivery device spacer includes a body including a plurality of device apertures and an arcuate slot defined therein. The plurality of device apertures includes two or more lumens each configured to receive an energy delivery device therethrough. The arcuate slot has a length, a width and a radius of curvature. The arcuate slot is configured to receive an additional energy delivery device therethrough.

The spacer may further include a plurality of ribs configured to form one or more air flow apertures. The ribs may connect the lumens and the arcuate slot. The body may also include a patient facing surface that includes at least one channel configured to space a portion of the patient facing surface away from patient tissue.

In a further embodiment, the radial center of the arcuate slot radius of curvature is related to the radial center of a lumen. One position along the length of the arcuate slot and two of the lumens may form a substantially straight line and the radial centers of two lumens and the radial center of the position along the length of the arcuate slot may be evenly spaced along the substantially straight line. Another position along the length of the arcuate slot and two of the lumens may form the corners of an isosceles triangle and another position along the length of the arcuate slot and two of the lumens may form the corners of an isosceles right triangle.

The body may include three lumens, each configured to receive a microwave energy delivery devices therethrough, and the radial centers of the three lumens may form the corners of an equilateral triangle.

In a further embodiment the device apertures formed by the body are substantially parallel and the microwave energy delivery devices inserted through the lumens and the arcuate slot may be substantially parallel.

In another embodiment of the present disclosure, an electrosurgical ablation system includes a microwave energy source, a plurality of microwave energy delivery devices and a microwave spacer. The microwave energy delivery devices each include a microwave antenna at a distal tip configured to receive microwave energy signals from the microwave energy source and to radiate microwave energy at a predetermined frequency. The microwave spacer includes a body including a plurality of device apertures defined therein. The device apertures may include two or more lumens and an arcuate slot having a length, a width and a radius of curvature. The lumens are each configured to receive one or more microwave energy delivery device therethrough.

The arcuate slot is configured to receive an additional microwave energy delivery device therethrough. The lumens and the arcuate slot are configured to guide microwave energy delivery devices.

The body may further include a plurality of ribs configured to form one or more air flow aperture. The ribs may connect the lumens and the arcuate slot.

In a further embodiment the body may include a patient facing surface with one or more channels configured to space a portion of the patient facing surface away from patient tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
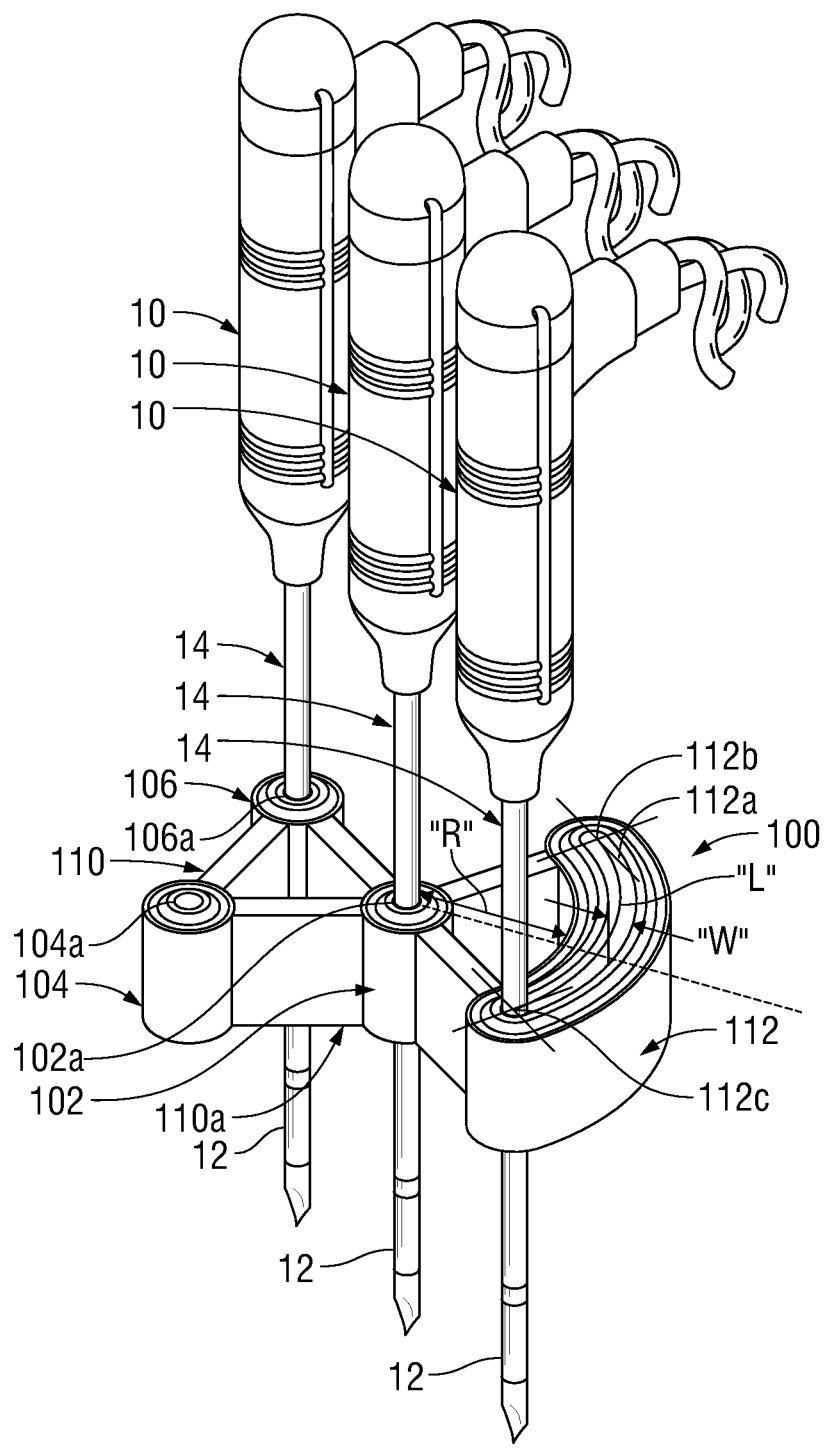
FIG. 1 is a perspective view of a microwave spacer, in accordance with the present disclosure that is configured to position three microwave energy delivery devices in a straight line configuration with a first spacing.
Figure 2:
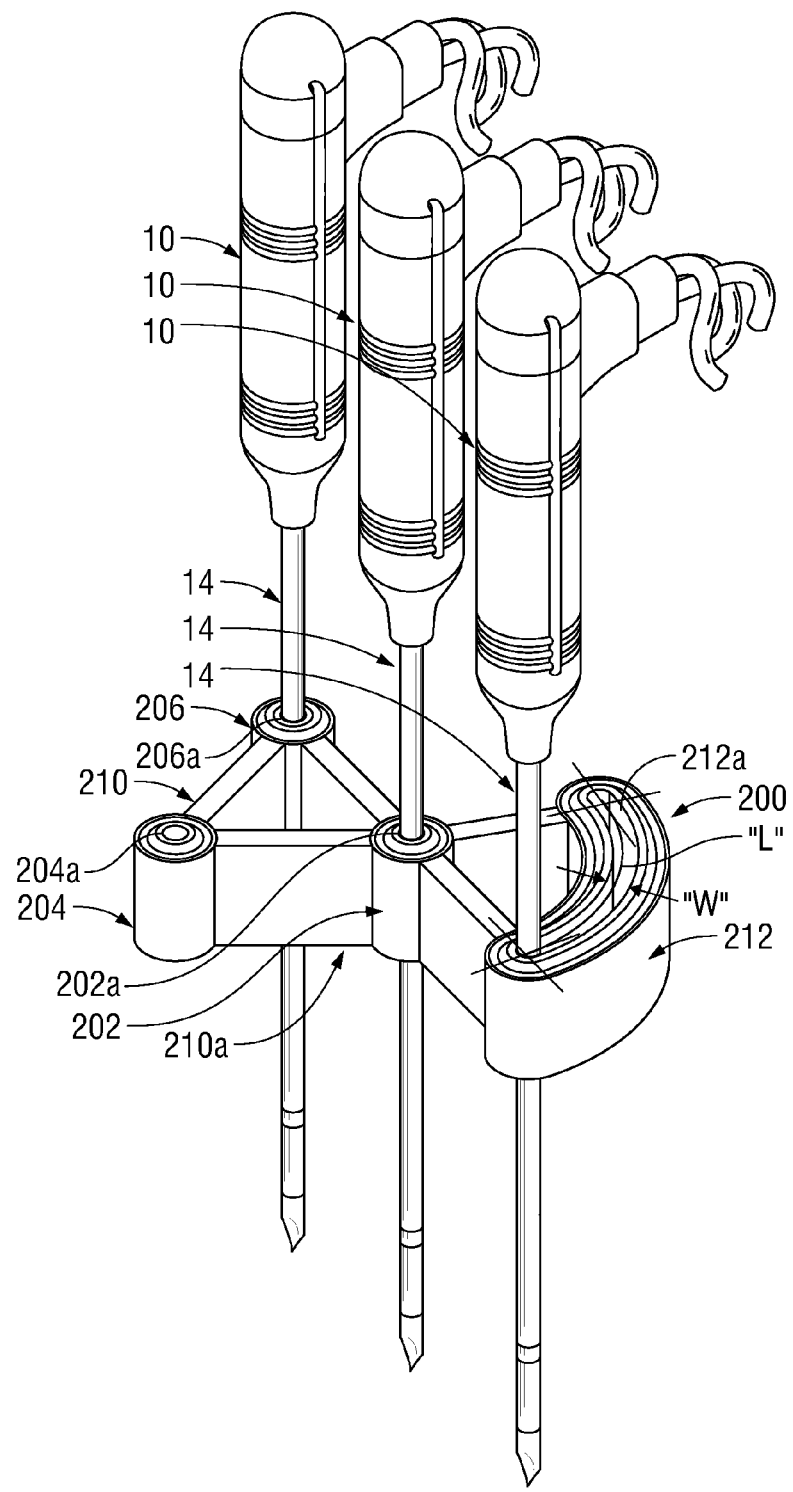
FIG. 2 is a perspective view of another embodiment of a microwave spacer, in accordance with the present disclosure that is configured to position three microwave energy delivery devices in a straight line configuration with a second spacing.

FIGS. 1 and 2 show perspective views of microwave spacers 100, 200 in accordance with one embodiment the present disclosure. Microwave spacers 100, 200 are generally constructed for use with a particular microwave energy delivery device 10. For example, the microwave energy delivery devices 10 illustrated in FIGS. 1 and 2 are penetrating microwave energy delivery devices sold by Covidien under the trademark Evident™ Microwave Ablation percutaneous antennas. Microwave spacers 100, 200 of the present disclosure may be adapted for use with any suitable tissue penetrating microwave energy delivery devices that include an antenna on the distal end and require controlled spacing therebetween. Microwave spacers 100, 200 of the present disclosure may be adapted for use with any suitable device that requires controlled spacing therebetween such as, for example, devices configure to deliver radio-frequency energy, ultrasonic energy, cryogenic energy, thermal energy, laser energy or any combination of devices or energy sources thereof.

Figure 3:
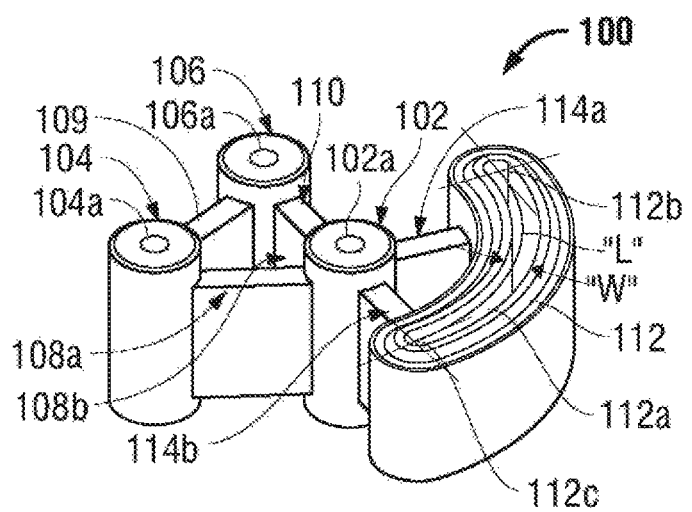
FIG. 3 is a perspective view of the microwave spacer of FIG. 1.
Figure 4:
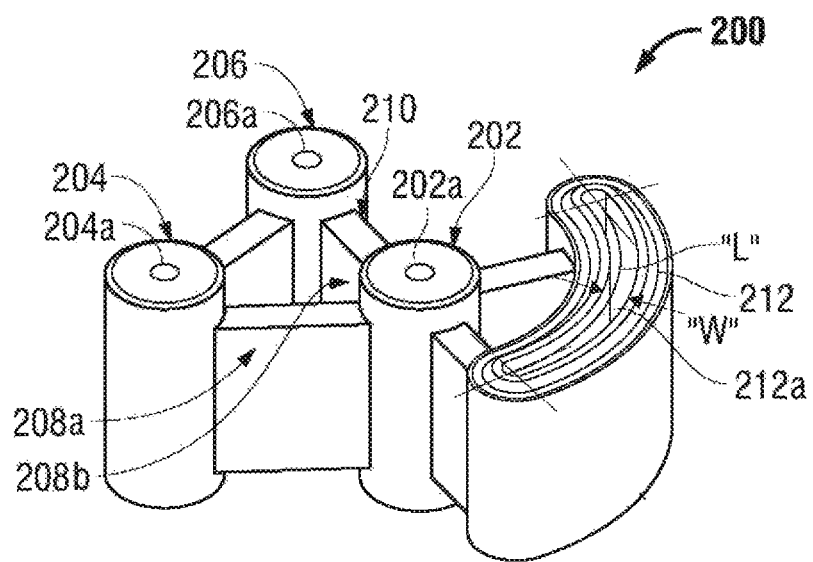
FIG. 4 is a perspective view of the microwave spacer of FIG. 2.

Each body 110, 210 of the respective microwave spacers 100, 200 forms a plurality of apertures that include a central tubular lumen 102a, 202a, a first side tubular lumen 104a, 204a, a second side tubular lumen 106a, 206a and an arcuate slot 112a, 212a defined therein that extend through each body 110, 210, respectively (see FIGS. 3 and 4). In this particular configuration the microwave spacers 100, 200 include three sets of fixed position apertures (i.e., the central tubular lumen 102a, 202a the first side tubular lumen 104a, 204a and the second side tubular lumen 106a, 206b) and one selectable aperture (i.e., arcuate slots 112a, 212a).

Figure 5B:
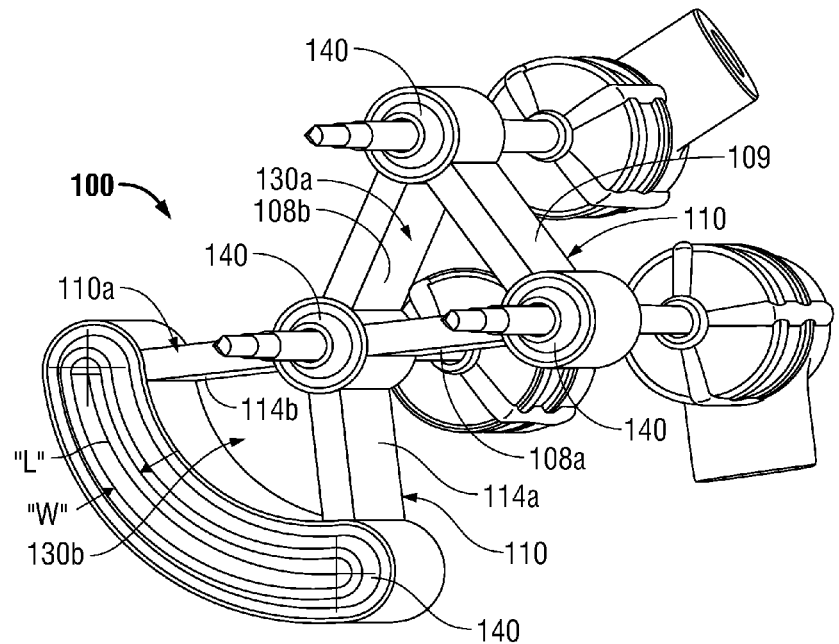
FIG. 5B is a perspective view of the patient facing surface of the microwave spacer of FIG. 1.
Figure 6:
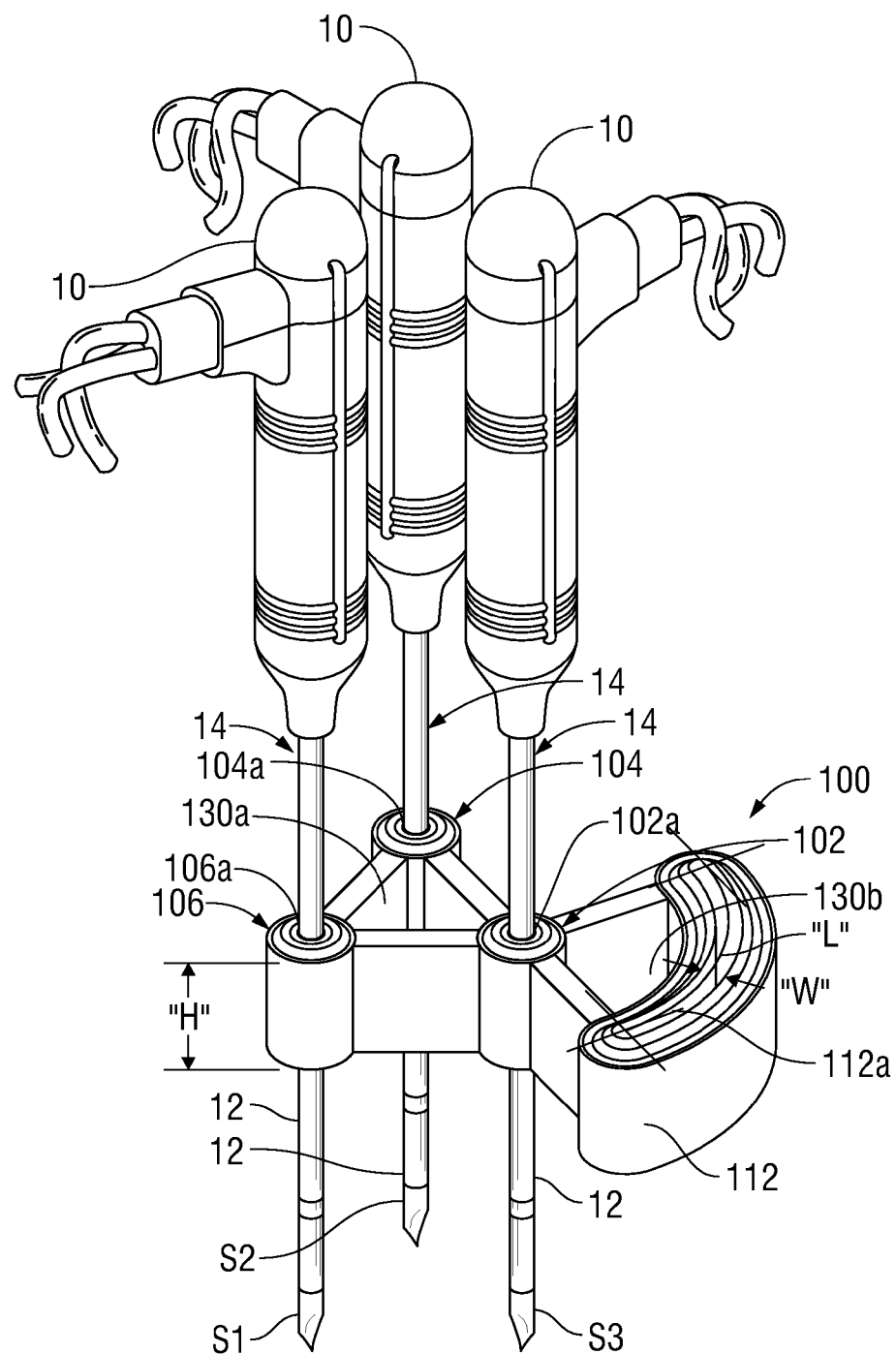
FIG. 6 is a perspective view of the microwave spacer of FIG. 1 in a configuration that positions the devices at the corners of an equilateral triangle.

In particular, microwave spacers 100, 200 are configured to arrange, align, position and/or configure the microwave energy delivery devices 10 for use in a surgical procedure. For example, microwave spacers 100, 200 are configured to arrange microwave energy delivery devices 10 in a substantially straight line or linear configuration (a linear configuration as shown in FIGS. 1 and 2, an equilateral triangular configuration as shown in FIGS. 5B and 6 or an isosceles triangle configuration forming an angle from between about 90° and 180°).

Each body 110, 120 of respective microwave spacers 100, 200 may form a plurality of device apertures therein and the apertures may include any combination of apertures types (i.e., fixed position apertures and/or selectable position apertures). For example, the first side tubular lumen 104a, 204a and the second side tubular lumen 106a, 206a may be replaced with a selectable position aperture, similar to the arcuate slot 112a, 212a, positioned radially outward from the central tubular lumen 102a, 202a. Another embodiment may include at least one arcuate slot and a plurality of fixed apertures or at least one fixed aperture and a plurality of arcuate slots.

Microwave spacers 100, 200 may include a plurality of sizes and/or spacing arrangements. For example, FIG. 1 illustrates a 1.5 cm microwave spacer 100 and FIG. 2 illustrates a 2.0 cm microwave spacer 200. The size of the microwave spacer 100, and/or the number and spacing of the fixed lumens 102a, 104a, 106a and/or the arcuate slot 112a may be related to the type of ablation device, a parameter related to the energy delivered by the ablation device (i.e., power, current, voltage and/or frequency of the energy), the type of surgical procedure performed and/or the length of the surgical procedure.

Patient facing surfaces 110a, 210a of respective microwave spacers 100, 200 face the patient and may be configured to facilitate contact with patient tissue. In one embodiment, a portion of the patient facing surface (e.g., surface 110a) includes a surface configured to aid in securing the microwave spacer 100 to patient tissue (i.e., a non-slip pattern formed in the body). In another embodiment, a portion of the patient facing surface 110a may include a coating or non-slip material configured to adhere to the patient, such as, for example, an adhesive coating, a non-skid cover or any other suitable surface or coating that aids in securing the microwave spacer 100 to the patient. In yet another embodiment, the microwave spacer (e.g., spacer 100) may include a plurality of appendages (i.e., feet and/or legs—not explicitly shown) or channels to elevate and/or space a portion of the patient facing surface 110a of the microwave spacer 100 with respect to patient tissue 160 (See FIG. 10).

For the purposes herein, microwave spacer 100 is described in further detail, however, it is contemplated that any of the features described herein may be applied to microwave spacer 200. The features of the microwave spacer 200 illustrated in FIG. 4 are labeled with like-numbers of corresponding features illustrated in FIG. 3.

Body 110 includes a plurality of apertures/fixed lumens 102a, 104a, 106a, 112a to guide at least a portion of the microwave energy delivery devices 10. The fixed apertures, which include the central tubular lumen 102a, the first side tubular lumen 104a and the second side tubular lumen 106a, position a microwave energy delivery device 10 in a fixed relationship with respect to the other fixed lumens 102a, 104a, 106a and microwave energy delivery devices 10 inserted therethrough. The adjustable apertures e.g., arcuate slot 112a, positions one or more microwave energy delivery devices 10 in an adjustable relationship with respect to the fixed lumens 102a, 104a, 106a.

Figure 5A:
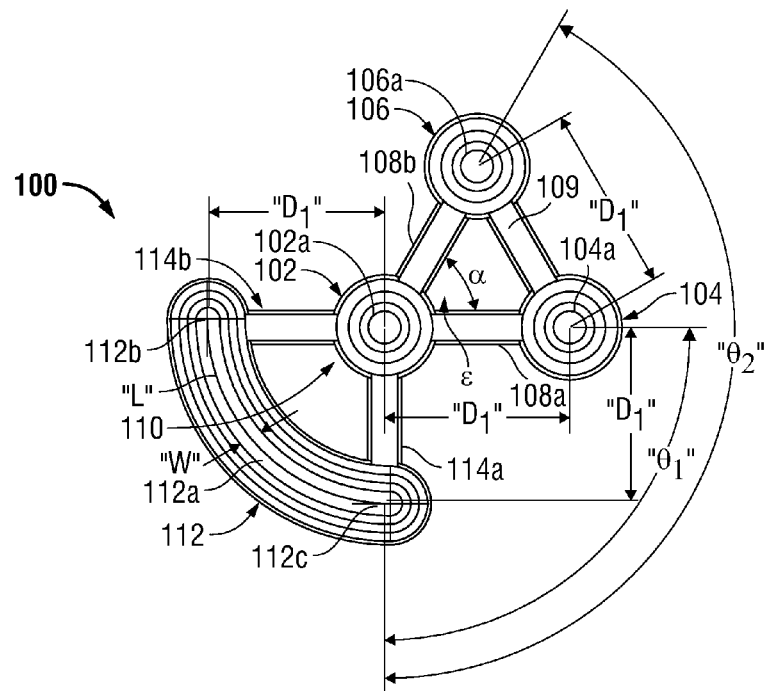
FIG. 5A is a bottom view of the microwave spacer of FIG. 1.

The arcuate slot 112a is configured to receive a microwave energy delivery device 10 through a plurality of positions along its length "L." The arcuate slot 112a is formed along a portion of an arc formed with a radial center positioned at the radial center of the central tubular lumen 102a and a radius of curvature (e.g., see FIG. 5A distance "D1"). The length "L" of the arcuate slot 112a is the circumferential length between the radial centers of microwave energy delivery devices inserted through the first end 112b and the second end 112c of the arcuate slot 112a. The width "W" is the width of the arcuate slot 112a measured along the radius "R." The width "W" is configured to receive a microwave energy delivery device 10 therethrough. The length of the arcuate slot 112a is selected such that a microwave energy delivery device may be positioned at a plurality of positions along the length "L" of the arcuate slot 112a to form a plurality of desirable configurations with respect the fixed lumens 102a, 104a, 106a, as described herein and illustrated in FIGS. 1, 5B and 7-9. In one embodiment, the radius of curvature of the arcuate slot 112a is selected such that radial center of the radius of curvature, formed by the arcuate slot 112a, is related to one of the fixed apertures, e.g., as illustrated in FIG. 1, the radial center of the arcuate slot 112a is the radial center of the central tubular lumen 102a.

With particular reference to FIGS. 3 and 4, microwave spacers 100, 200 include a central stem 102, 202 defining a central tubular lumen 102a, 202a therethrough. Microwave spacers 100, 200 further include a first side tubular stem 104, 204 defining first side tubular lumen 104a, 204a therethrough, and second side tubular stems 106, 206 defining a second side tubular lumen 106a, 206a therethrough. First side tubular stems 104, 204 are connected to respective central stems 102, 202 by a first bridge 108a, 208a and second side tubular stem 106, 206 is connected to central stem 102, 202 by a second bridge 108b, 208b.

As illustrated in FIG. 5A, the first bridge 108a, 208a and second bridge 108b, 208b are off-set or angled from one another by an angle "a." equal to 60°. First side tubular lumen 104a, 204a of first side tubular stem 104, 204 and second side tubular lumen 106a, 206a of second side tubular stem 106, 206 are each spaced from central tubular lumen 102a, 202a of central stem 102, 202 by an equivalent distance "D1." The distance "D1" may relate to the type of ablation device, a parameter related to the energy delivered by the ablation device (i.e., power, current, voltage and/or frequency of the energy), the type of surgical procedure performed and/or the length of the surgical procedure. In one embodiment, the distance "D1" is equal to about 0.591 in.

Microwave spacer 100 may be configured such that fixed lumens 102a, 104a and 106a of respective tubular stems 102, 104 and 106 are parallel with respect to one another. Additionally, each fixed lumen 102a, 104a and 106a of respective tubular stems 102, 104 and 106 may be sized and dimensioned to slideably receive a shaft 14 (see FIGS. 1 and 2) of a particularly-sized microwave energy delivery device 10.

FIG. 5B is a perspective view of the patient facing surface 110a of the microwave spacer 100. Patient facing surface 110a may include one or more legs 140 to elevate a portion of the body 110 with respect to patient tissue (not explicitly shown) thereby allowing air to freely flow between the patient and at least a portion of the patient facing surface 110a (i.e., exterior bridge 109, first bridge 108a, second bridge 108b, first guide body support bridge 114a and second guide body support bridge 114b.) In use, thermal energy generated at the surface of the patient tissue (not explicitly shown) dissipates through the first airflow aperture 130a and/or the second airflow aperture 130b. As heat is generated at the tissue surface (i.e., tissue directly below the patient facing surface 110a of the microwave spacer 100), a convection air current is generated wherein heated air, within the first airflow aperture 130a and/or second airflow aperture 130b, rises. This convection air current draws fluid through the space formed between the patient facing surface 110a and patient tissue.

With continued reference to FIGS. 3-5B, microwave spacer 100 further includes an arcuate guide body 112 defining an arcuate slot 112a therethrough. Arcuate guide body 112 is connected to central stem 102 by a first guide body support bridge 114a and a second guide body support bridge 114b. Second guide body support bridge 114b is axially-aligned with first bridge 108a. First guide body support bridge 114a is oriented at an angle "θ1" relative to first bridge 108a and oriented at an angle "θ2" with respect to second bridge 108b. In one embodiment the angle "θ1" is about 90° and the angle "θ2" is about 150°.

A first end 112b of arcuate slot 112a of arcuate guide body 112 is axially aligned with first side tubular lumen 104a of first side tubular stem 104. A second end 112c of arcuate slot 112a is oriented at an angle "θ1" relative to first side tubular lumen 104a of first side tubular stem 104 and is oriented at an angle "θ2" with respect to second side tubular lumen 106a of second side tubular stem 106. First end 112b of arcuate slot 112a of arcuate guide body 112 and second end 112c of arcuate slot 112a of arcuate guide body 112 are each spaced from central tubular lumen 102a of central stem 102 by an equivalent distance "D1."

With reference to FIG. 5A, arcuate slot 112a of arcuate guide body 112 defines a radius of curvature having its center located along the central axis of central stem 102 and that is parallel to fixed lumens 102a, 104a and 106a of respective tubular stems 102, 104 and 106. Additionally, arcuate slot 112a of arcuate guide body 112 is sized and dimensioned to slidably receive a shaft 14 of a microwave energy delivery device 10 therethrough, as illustrated in FIGS. 1 and 2.

With reference to FIG. 6, tubular stems 102, 104 and 106, and arcuate guide body 112 have a height "H" that is sufficient to maintain substantial parallelism of the shafts 14 of the microwave energy delivery devices 10 inserted into the respective fixed lumens 102a, 104a, 106a and arcuate slot 112a thereof. The height "H" is sufficiently long to guide the microwave energy delivery devices 10 such that the distal ends of the devices are positioned in a desirable spaced apart relationship relative to each other such that the spacing of the distal tips S1, S2 and S3 are desirably spaced and the spacing between the distal tips S1, S2 and S3 is substantially equal.

In another embodiment, the shafts 14 of the microwave energy delivery devices 10 are not substantially parallel to each other. As such, the spacing between the distal tips S1, S2 and S3 may increase or decrease as the microwave energy delivery devices 10 are inserted through the microwave spacer 100.

Microwave spacer 100 may be constructed from any suitable material, such as a non-conductive plastic material (e.g., nylon or polyamide) or a ceramic.

Microwave spacer 100 is configured to provide a plurality of microwave energy delivery device 10 orientations with varying spacing between each microwave energy delivery device 10. FIGS. 1 and 2 illustrate a straight line configuration of the microwave energy delivery devices 10. Additional orientations and spacing between microwave energy delivery devices 10 are further illustrated in FIGS. 5B, and 6-9.

In FIGS. 5B and 6, the three fixed lumens 102a, 104a, 106a position the radial centers of the microwave energy delivery devices 10 such that the radial centers form the corners of an equilateral triangle, wherein the sides of the triangle are equal to a distance "D1," as illustrated in FIG. 5A and the equilateral triangle angle "β" is equal to 60°.

Figure 7:
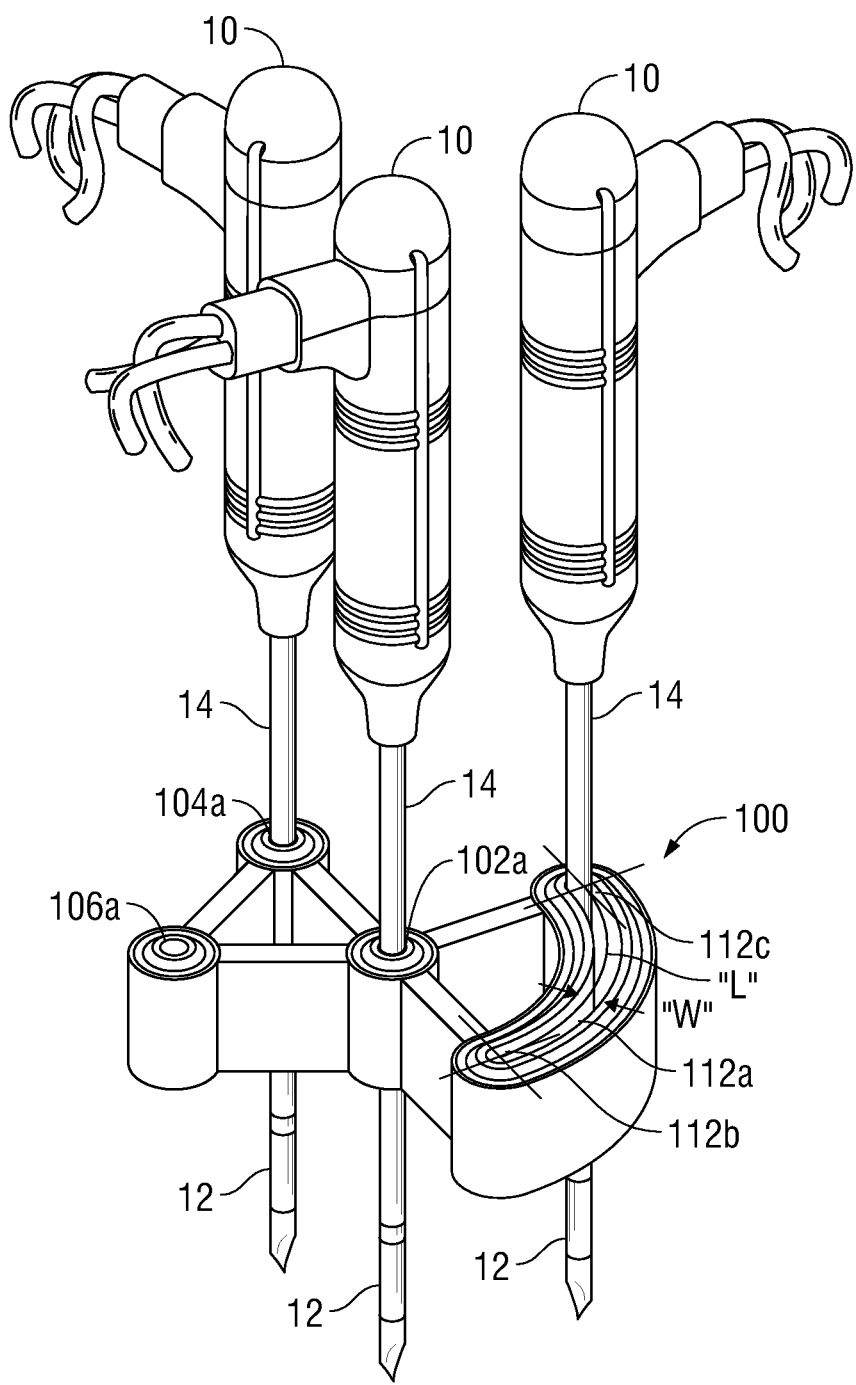
FIG. 7 is a perspective view of the microwave spacer of FIG. 1 in a configuration that places the devices at the corners of a first isosceles triangle.

In FIG. 7, central tubular lumen 102a, first side tubular lumen 104a and the second end 112c of the arcuate slot 112a position the radial centers of the shafts 14 of the microwave energy delivery devices 10 such that the radial centers form the corners of a right isosceles triangle with angles of 90°, 45° and 45°.

Figure 8:
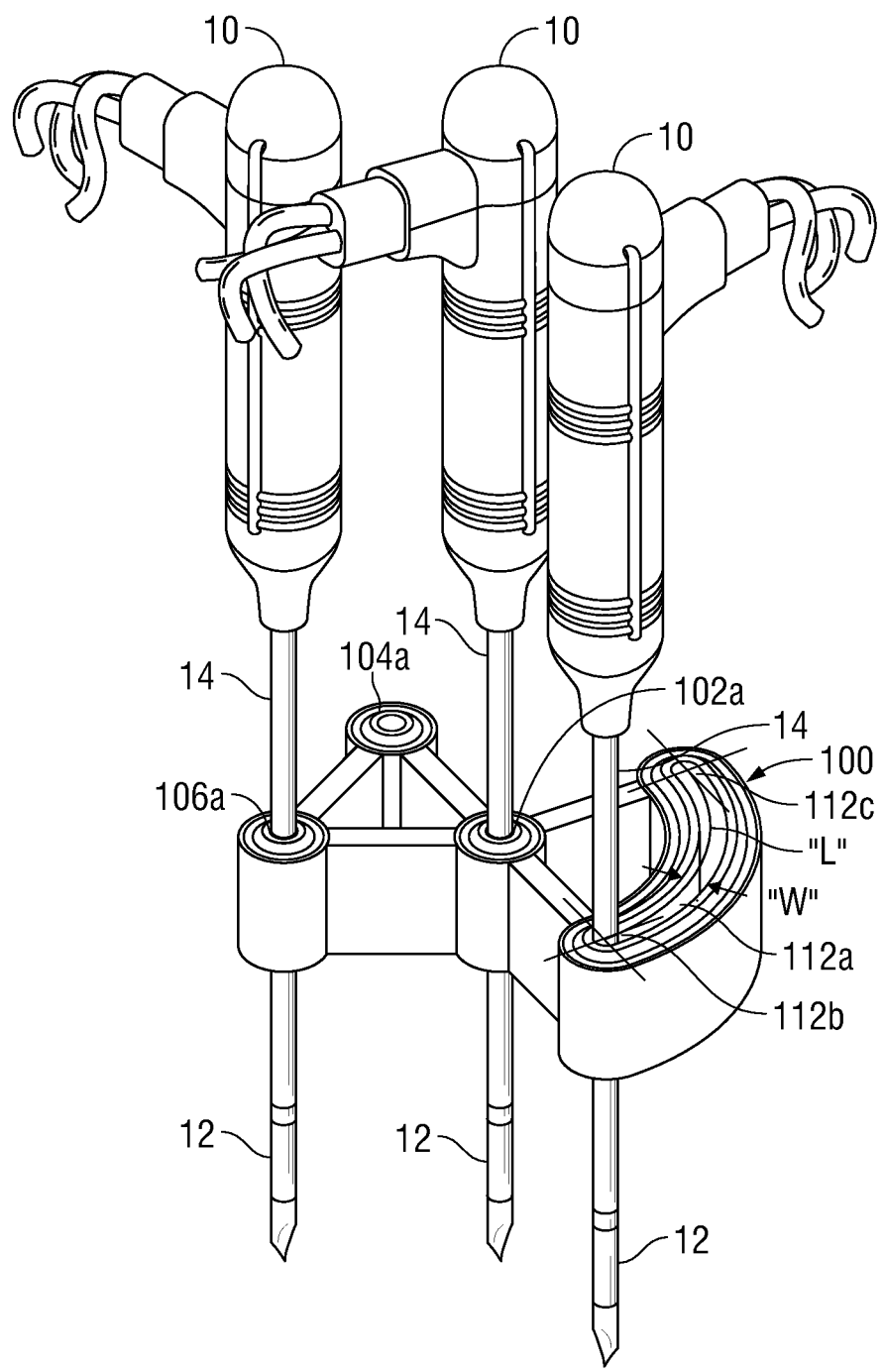
FIG. 8 is a perspective view of the microwave spacer of FIG. 1 in a configuration that places the devices at the corners of a second isosceles triangle.

In FIG. 8, central tubular lumen 102a, second side tubular lumen 106a and the first end 112b of the arcuate slot 112a position the radial centers of the shafts 14 of the microwave energy delivery devices 10 such that the radial centers form the corners of an obtuse triangle with angles of 120°, 30° and 30°.

Figure 9:
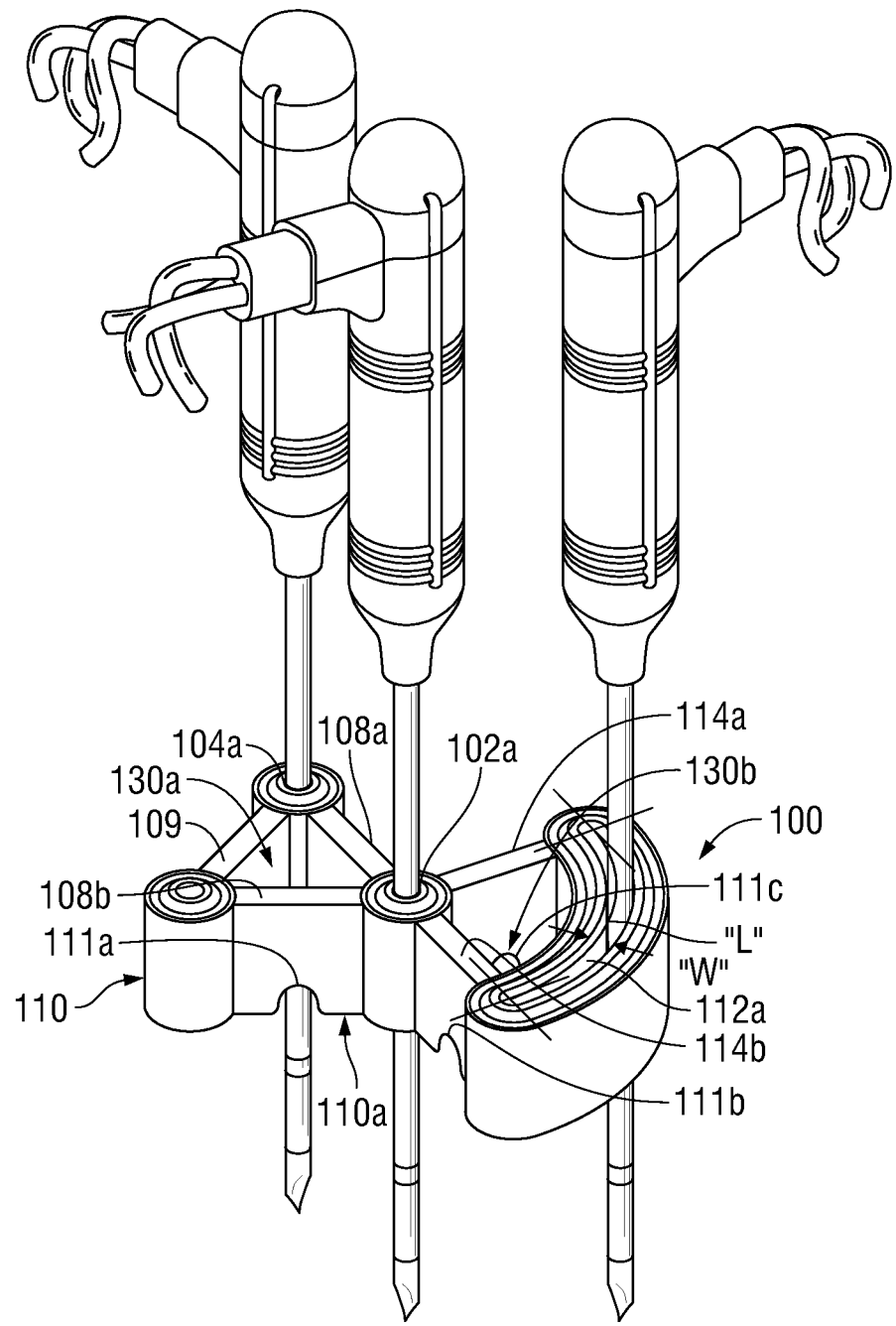
FIG. 9 is a top, perspective view of the microwave spacer of FIG. 1 with a microwave energy delivery device positioned in a selected position along the length of an arcuate slot defined within the spacer.

FIG. 9 illustrates that the shaft 14 of the microwave energy delivery device 10 inserted into arcuate slot 112a may be positioned at any point along the length of the arcuate slot 112a, thereby providing a plurality of configurations in which the microwave energy delivery devices 10 may be arranged.

With continued reference to FIG. 9, bridges 108a, 108b, 109, 114a, 114b provide structural strength to the microwave spacer 100 thereby preventing deflection and/or preventing the microwave spacer 100 from changing shape or form. In addition, first bridge 108a, second bridge 108b and exterior bridge 109 of the body 110 form the sides of a first airflow aperture 130a. First guide body support bridge 114a, second guide body support bridge 114b and arcuate guide body 112 form the sides of a second airflow aperture 130b. First airflow aperture 130a and second airflow aperture 130b are configured to allow heat (generated at the surface of the patient tissue) to dissipate through the microwave spacer 100. The body 110 may include one or more passageways, such as first airflow aperture 130a or second airflow aperture 130b, for air to flow between the patient facing surface 110a and patient tissue (not explicitly shown). Thermal energy generated at the surface of the patient tissue (not explicitly shown) dissipates through the first airflow aperture 130a and/or the second airflow aperture 130b. Body 110 of the microwave spacer 100 may be formed from a light weight material resistant to thermal heating.

In yet another embodiment of the present disclosure the patient facing surface 110a may include one or more channels 111a, 111b, 111c formed therein. Channels 111a, 111b, 111c form a fluid pathway for air to flow between the patient facing surface 110a and patient tissue (not explicitly shown). As heat is generated at the tissue surface (i.e., tissue directly below the patient facing surface 110a of the microwave spacer 100), a convection air current is generated wherein the heated air, within the first airflow aperture 130a and/or second airflow aperture 130b, rises. In turn, the convection air current draws fluid into the first airflow aperture 130a and/or the second airflow aperture 130b through the channel 111a, 111b, 111c respectively. Each bridge 108a, 108b, 109, 114a and 114b may include one or more channels, formed along the patient facing surface 110a, to provide a fluid pathway for a convection air current to flow.

Figure 10:
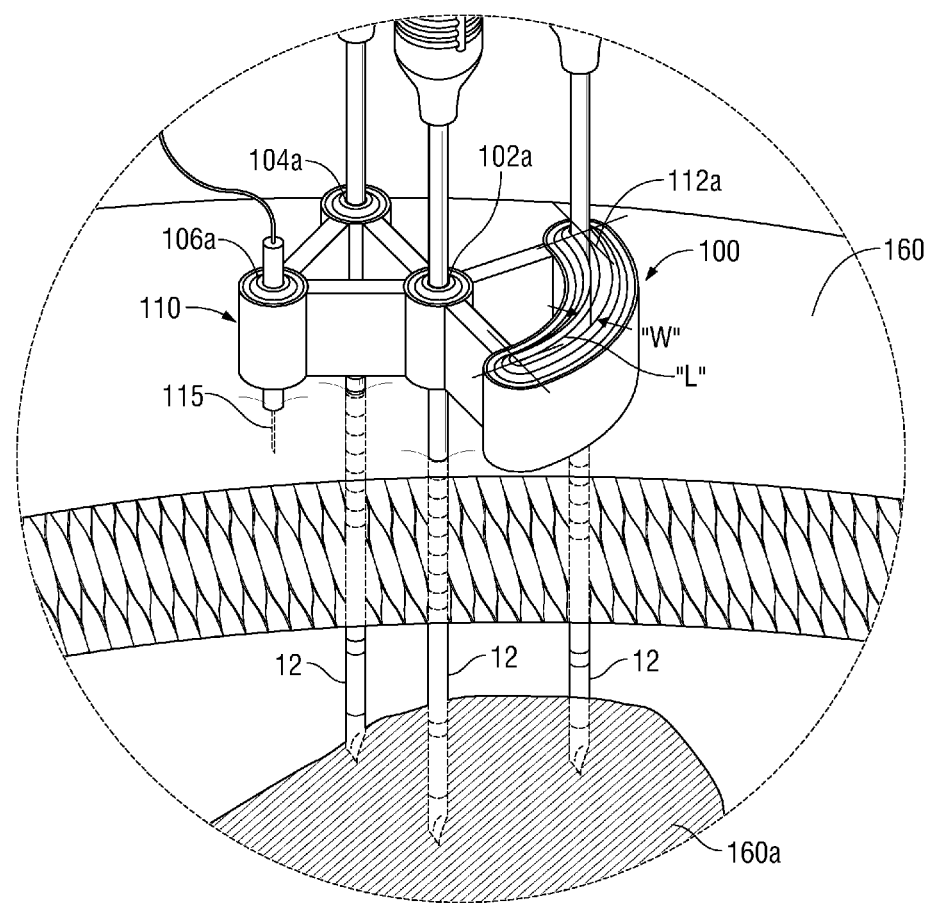
FIG. 10 is a top, perspective view of the microwave spacer positioned on patient tissue with the distal portions of the microwave energy delivery devices inserted in target tissue.

In use, as illustrated in FIG. 10, a microwave spacer 100 is placed on patient tissue 160 adjacent a target tissue 160a or tissue targeted for a medical procedure, (i.e., an ablation procedure, a resection procedure or any other suitable electrosurgical procedure that requires electrosurgical energy delivery). The clinician may utilize an imaging/positioning system, such as, for example, an ultrasonic system, an x-ray system, a CT scan or any other suitable imaging/positioning system (not explicitly shown) to determine proper positioning of the microwave spacer 100 with respect to the target tissue 160a. Each of the microwave energy delivery devices 10 is inserted into a selected fixed lumen 102a, 104a and/or a selected position of the arcuate slot 112a. The imaging system (not explicitly shown) may be used during the insertion step to determine when each microwave energy delivery device 10 is properly positioned in target tissue 160a. The microwave ablation procedure may require the use of any number and/or combination of fixed lumens 102a, 104a, 106a and/or arcuate slot 112a. Apertures not used for the insertion of microwave energy delivery devices 10 May be used for the placement of a probe or sensor configured to measure a property of the target tissue such as, for example, a temperature (i.e., thermocouple, RTD or inferred heat measuring device), impedance and/or a tissue fluid content.

A method for placing a plurality of microwave energy delivery devices 10 and ablating tissue is also provided by the present invention and includes the steps of placing the microwave spacer 100 on a portion of patient tissue 160 adjacent a target tissue 160a; inserting two or more microwave energy delivery devices 10 through fixed lumens 102a, 104a, 106a formed in the body 110 of the microwave spacer 100 into the target tissue 160a; selecting a position on the arcuate slot 112a; inserting at least one microwave energy delivery device 10 through the arcuate slot 112a into the target tissue 160a; connecting the three or more microwave energy delivery devices 10 to a microwave energy source (not explicitly shown); ablating the target tissue 160a by delivering microwave energy through the microwave energy delivery devices 10; and cooling patient tissue 160 by providing airflow through a plurality of airflow apertures formed through the body 110 of the microwave spacer 100.

Another method for placing a plurality of microwave energy delivery devices 10 and ablating tissue includes the steps of: placing the microwave spacer 100 on a portion of patient tissue 160 adjacent a target tissue 160a; inserting two or more microwave energy delivery devices 10 through fixed apertures formed in the body 110 of the microwave spacer 100; advancing an antenna 12 of the microwave energy delivery devices 10 to the target tissue 160a; inserting another microwave energy delivery device 10 in a selected insertion position in an arcuate slot 112a forming in the body 110 of microwave spacer 100 and into the target tissue; connecting the microwave energy delivery devices 10 to a microwave energy source; and ablating the target tissue by delivering microwave energy through the microwave energy delivery devices 10.

The methods may further include the step of cooling the patient's tissue by providing airflow through a plurality of channels 111a, 111b, 111c formed in the body 110 of the microwave spacer 100.

One or more of the afore described methods may further include the step of inserting one or more sensors 115 through a lumen (i.e., fixed lumens 102a, 104a, 106a, as illustrated in FIG. 10, or a selected position on arcuate slot 112a) formed in the body 110 of the microwave spacer 100 into the target tissue. The sensor 115 may be configured to measure a property of the target tissue such as, for example, a temperature (i.e., thermocouple, RTD or inferred heat measuring device), impedance and/or a tissue fluid content.

FIGS. 11A-14 show various views of a pivotable microwave spacer 300 in accordance with the present disclosure. Pivotable microwave spacer 300 is generally constructed for use with a particular microwave energy delivery device 10. For example, the microwave energy delivery devices 10 illustrated in FIGS. 11A, 11B, 13 and 14 are sold by Covidien under the trademark Evident™ Microwave Ablation percutaneous antennas. Pivotable microwave spacer 300 of the present disclosure may be adapted for use with any suitable device that requires controlled spacing therebetween such as, for example, devices configured to deliver radio-frequency energy, ultrasonic energy, cryogenic energy, thermal energy, laser energy or any combination of devices or energy sources thereof.

The body 310 of the pivotable microwave spacer 300 includes a first body 311 and a second body 312 pivotally attached thereto. First body 311 includes an upper first body member 311a, a lower first body member 311b and a first body spacer 311c. Second body 312 includes a second body member 312a and a second body stop 312b. Upper first body member 311a and lower first body member 311b each form a portion of the pivot aperture 304 therein. Second body member 312a forms a second body pivot aperture 304b therein disposed in vertical registration with respect to first body pivot aperture 304a formed in the first body 311. First body pivot aperture 304a and second body pivot aperture 304b pivotally attach the first body 311 and second body 312 about the pivot aperture 304.

Figure 11A:
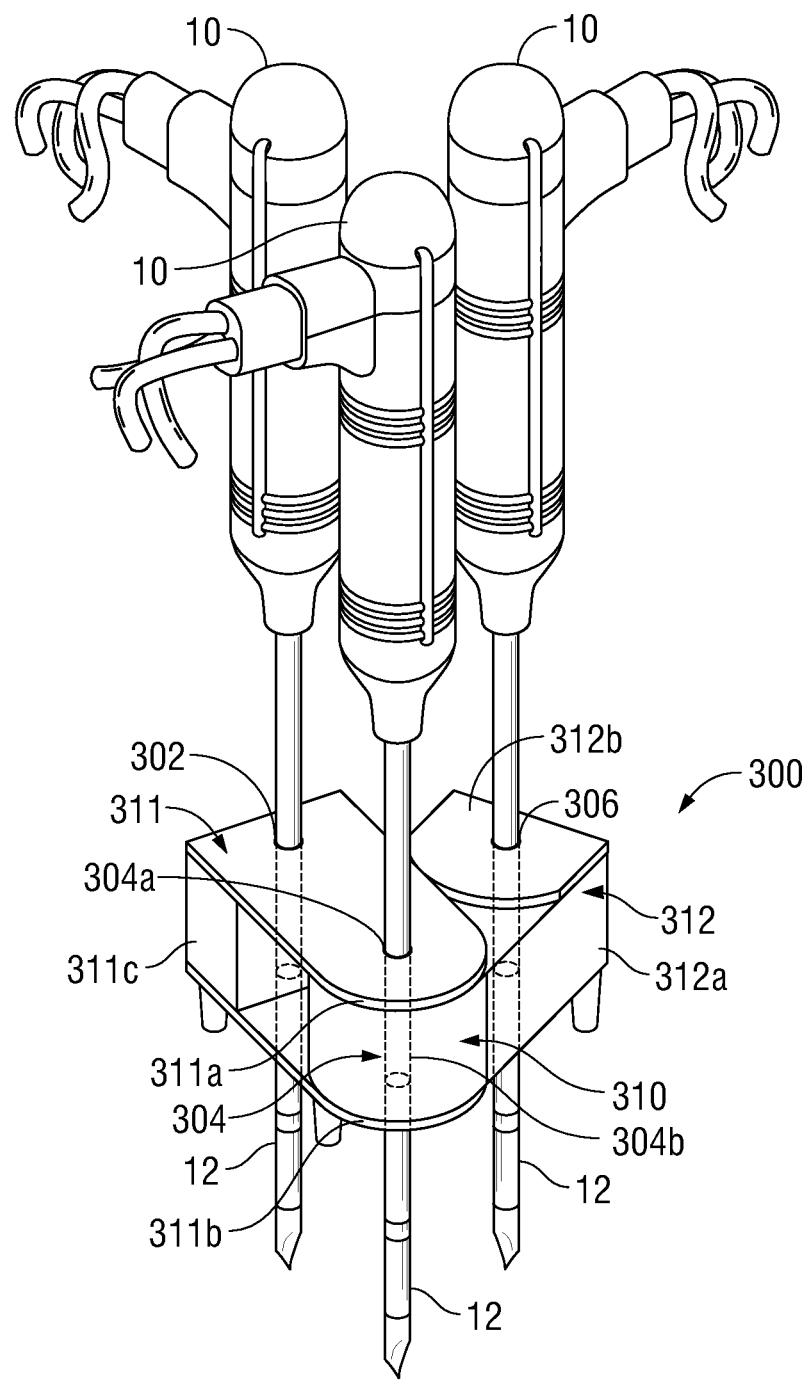
FIG. 11A is a perspective view of a pivotable microwave spacer, in accordance with another embodiment of the present disclosure that is configured to position three microwave energy delivery devices at the corners of an equilateral triangle.

As illustrated in FIG. 11A, the first body 311 forms a first body aperture 302 and the second body 312 forms a second body aperture 306. In this particular embodiment the first body aperture 302, the pivot aperture 304 and the second body aperture 306 are equally spaced from each other thereby forming the corners of an equilateral triangle. In another embodiment, first body 311 and/or second body 312 of the pivotable microwave spacer 300 may form two or more apertures therein. For example, in one embodiment the first body 311 and/or the second body 312 form at least two apertures therein and form a pivotable microwave spacer 300 for positioning microwave energy delivery devices 10 along a resection line wherein the resection line includes at least one variable angle.

As illustrated in FIG. 11A, the angular relationship between the first body 311 and second body 312 is adjustable between a minimum angular relationship and a maximum angular relationship. The size and/or position of the second body stop 312b determine the maximum and minimum angular relationship between the first body 311 and the second body 312. For example, in FIG. 11A the second body stop 312b limits the angular relationship between the first body 311 and the second body 312 between about 60° and about 300°, wherein the second body stop 312b makes contact with the upper first body member 311a at the minimum and maximum angular relationships between the first body 311 and second body 312. In another embodiment, the second body stop 312b limits the angular relationship between the first body 311 and the second body 312 between about 30° to about 330°. In yet another embodiment, the second body stop 312b limits the angular relationship between the first body 311 and second body 312 between about 60° and 270° wherein at 60° the centers of the apertures 302, 304, 306 form the corners of an equilateral triangle and at 270° form the corners of an isosceles right triangle wherein a right angle is formed at the pivot aperture 304 (composed of first body pivot aperture 304a and second body pivot aperture 304b.

Figure 11B:
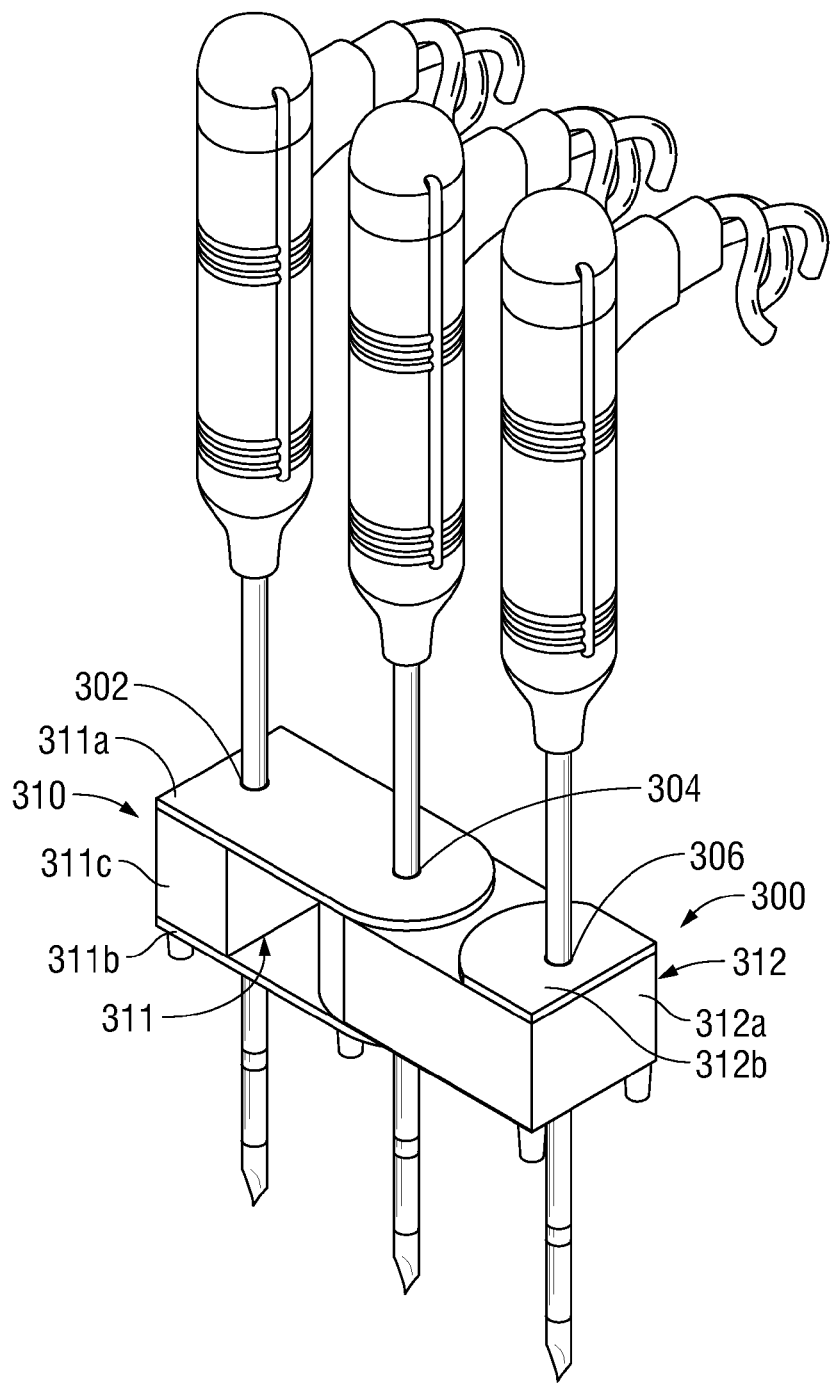
FIG. 11B is a perspective view of the pivotable microwave spacer of FIG. 11A configured to position three microwave energy delivery devices in a straight line configuration.

In another position, as illustrated in FIG. 11B, the first body 311 and second body 312 are positioned at 180° with respect to each other, wherein the first body aperture 302, second body aperture 306 and pivot aperture 304 form a substantially straight line therebetween. FIGS. 11A and 11B illustrate only two positions of a plurality of angular positions wherein the angle between the first body 311 and the second body 320 varies between about 60° and about 300°.

Figure 12A:
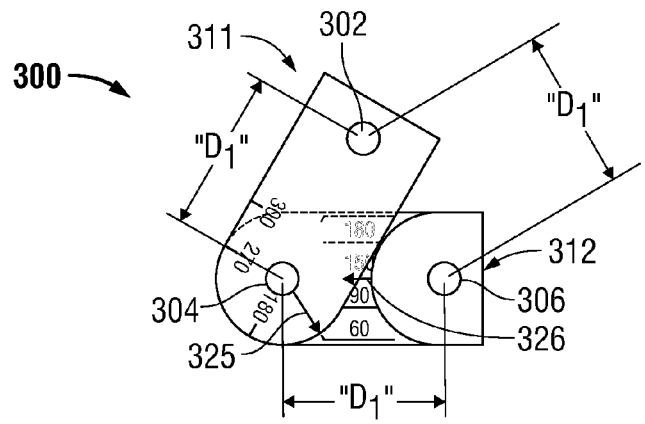
FIGS. 12A-12C are top views of the pivotable microwave spacer of FIG. 11A in various angular positions.
Figure 12B:
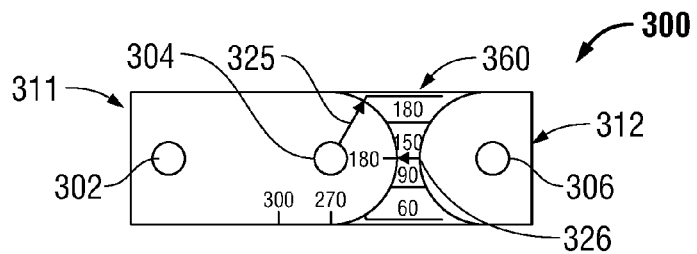
Figure 12C:
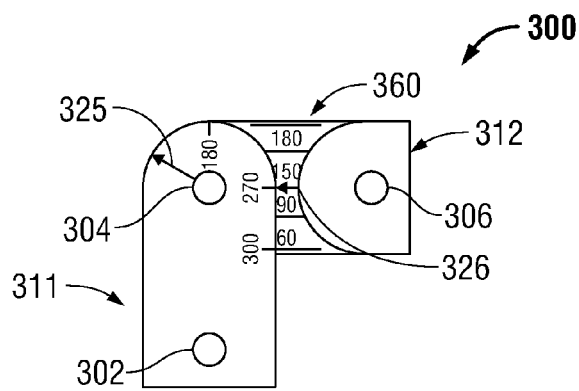

The angular relationship between the first body 311 and the second body 312 of the pivotable microwave spacer 300 may be determined by providing an angular gauge 360 as illustrated in FIGS. 12A-12C and described hereinbelow. The pivotable microwave spacer 300 illustrated in FIGS. 12A-12C is configured to provide adjustability between 60° and 300°. An angular gauge 360, as described herein, may be adapted to provide the angular relationship of any such pivoting microwave spacer.

Angular gauge 360 includes a first angular indicator 325 and a second angular indicator 326. First angular indicator 325 provides angular measurements between 60° and 180° and second angular indicator 326 provides measurements between 180° and 300°. FIG. 12A illustrates the angular relationship between the first body 311 and second body 312, as indicated by the first angular indicator 325, equal to 60° (pivoted fully counter-clockwise with the first body 311 in contact with the second body stop 312b). FIG. 12B illustrates the angular relationship between the first body 311 and the second body 312, as measured by the first angular indicator 325 and/or the second angular indicator 326, equal to 180° (longitudinal side edges of First body 311 and second body 312 in alignment). FIG. 12C illustrates the angular relationship between the first body 311 and the second body 312, measured by the second angular indicator 326, equal to 270°. Angular gauge 360 indicates the angular position between the first body 311 and the second body 312 through the entire range of rotation between the first body 311 and the second body 312.

Figure 13A:
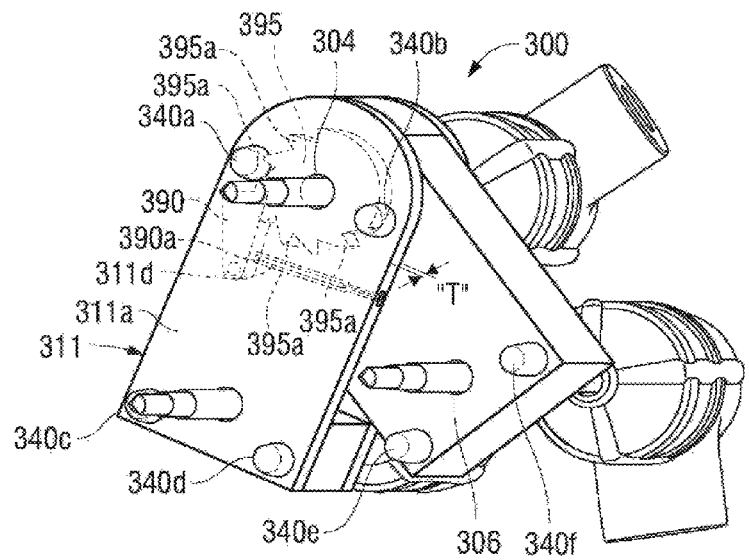
FIG. 13A is a bottom, perspective view of the patient facing surface of the pivotable microwave spacer of FIG. 11A including an embodiment of a locking/holding mechanism.
Figure 13B:
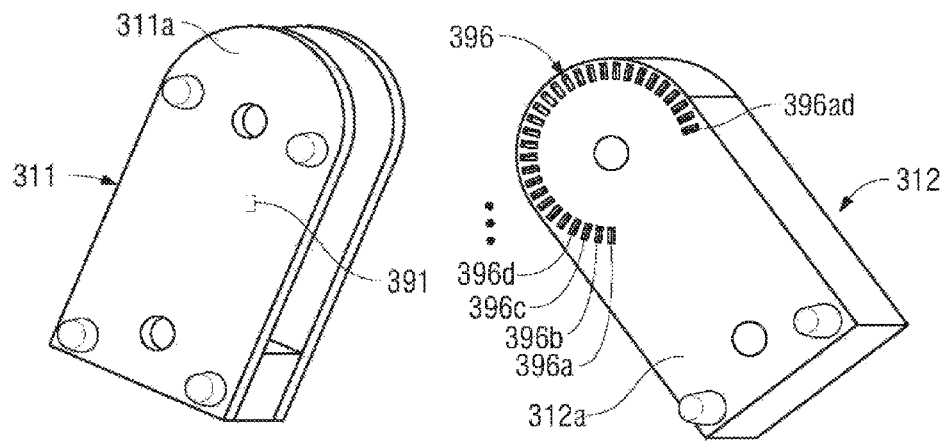
FIG. 13B is a bottom, perspective view of the patient facing surface of components of the pivotable microwave spacer of FIG. 11A including another embodiment of a locking/holding mechanism.

In a further embodiment, as illustrated in FIGS. 13A and 13B, pivotable microwave spacer 300 may further include a locking and/or holding mechanism (e.g., ratchet 395 and catch 390 or notch or protuberance 391 and recessed channels 396) to lock and/or hold the first body 311 in a desirable position with respect to the second body 312. Ratchet 395 includes a plurality of ratchet teeth 395a configured to engage catch 390. Catch 390 is biased against ratchet 395 and engages one or more ratchet teeth 395a or any portion of the ratchet 395 thereby preventing further rotation of the first body 311 with respect to the second body 312. Catch release 390a, positioned in catch release aperture 311d formed in the first body 311, when pressed disengages the catch 390 from the ratchet 395.

As illustrated in FIG. 13B, the first body 311 and second body 312 include mechanically interfacing surfaces configured to engage and/or lock the first body 311 in a desirable position with respect to the second body 312. For example, upper first body member 311a of the first body 311 may form a notch 391 that engages at least one of a plurality of recessed channels 396a-396ad formed in the second body member 312a of the second body 312. When assembled, notch 391 aligns with the plurality of recessed channels 396 and incrementally engages the recessed channels (e.g., engages recessed channel 396a and subsequently engages channel 396b, etc. . . . ) as the position of the first body 311 is adjusted with respect to the second body 312. In a further embodiment, recessed channels 396a-396ad may be incrementally spaced, such as, for example, spaced in 10° intervals as illustrated in FIG. 13B.

In a further embodiment, as illustrated in FIG. 13, pivotable microwave spacer 300 may include a plurality of legs 340a-340f configured to facilitate contact with the patient. Legs 340a-340f are configured to elevate at least a portion of the pivotable microwave spacer 300 such that the pivotable microwave spacer 300 is substantially parallel to patient tissue. In one embodiment, feet 340e, 340f are only included on the second body 312 wherein each foot e.g., foot e.g., foot 340e, 340f, elevates the second body 312 the thickness "T" of the lower first body member 311b. Legs 340a-340f may include a coating or non-slip material that adheres to the patient, such as, for example, an adhesive coating, a non-skid cover or any other suitable surface or coating that aids in securing the pivotable microwave spacer 300 to the patient.

In another embodiment, the pivotable microwave spacers 300 may include an arcuate slot or non-arcuate slot as described hereinabove.

Figure 14:
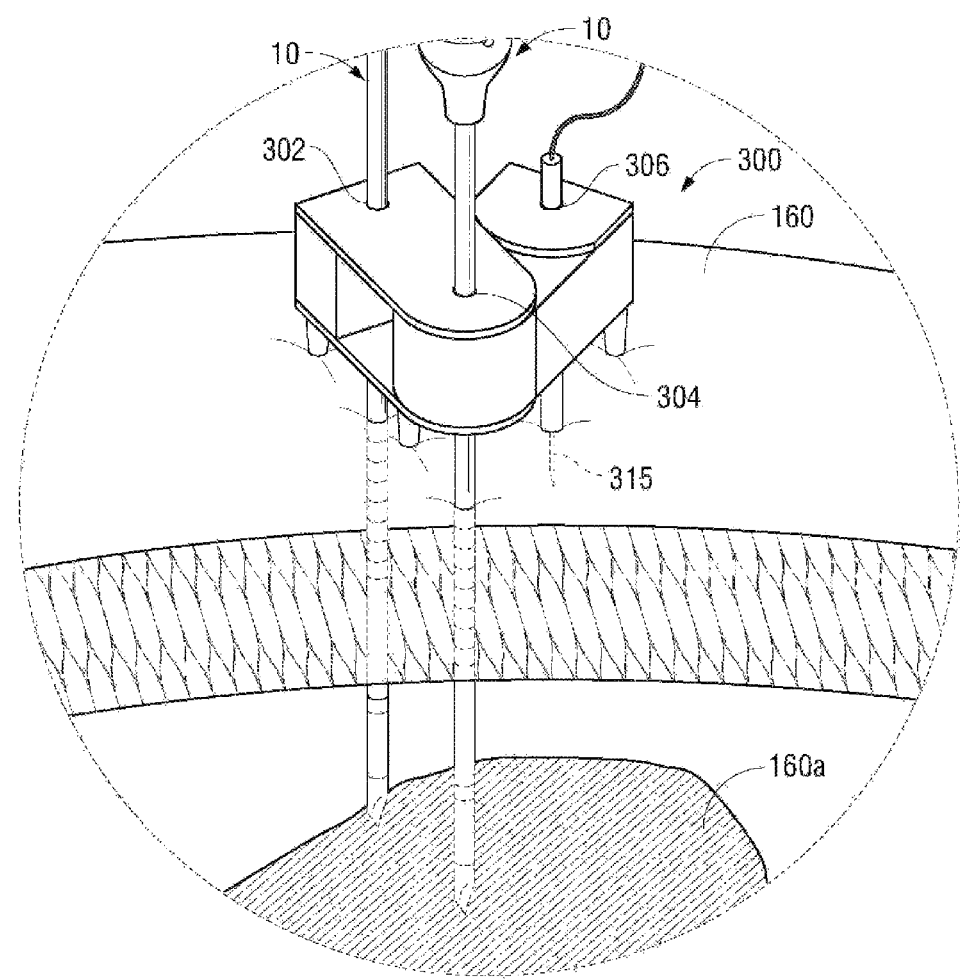
FIG. 14 is a top, perspective view of the pivotable microwave spacer of FIG. 11A positioned on patient tissue with the distal portion of the microwave energy delivery devices inserted in target tissue.

In use, as illustrated in FIG. 14, pivotable microwave spacer 300 is placed on patient tissue 160 adjacent a target tissue 160a e.g., tissue targeted for a medical procedure, (i.e., an ablation procedure, a resection procedure or any other suitable electrosurgical procedure that requires electrosurgical energy delivery). The clinician may utilize an imaging/positioning system, such as, for example, an ultrasonic system, an x-ray system, a CT scan or any other suitable imaging/positioning system (not explicitly shown) to determine proper positioning of the pivotable microwave spacer 300 with respect to the target tissue 160a. Each of the microwave energy delivery devices 10 is inserted into a respective aperture 302, 304, 306 and into patient tissue 160. An imaging system (not explicitly shown) may be used during the insertion step to determine when each microwave energy delivery device 10 is properly positioned in target tissue 160a. Apertures not used for the insertion of microwave energy delivery devices 10 may be used for the placement of a sensor 115 configured to measure a property of the target tissue such as, for example, a temperature (i.e., thermocouple, RTD or inferred heat measuring device), impedance and/or a tissue fluid content.

In yet another embodiment, a microwave spacer (not shown) in the spirit of the present disclosure is formed by including three or more bodies that form an interlocking microwave spacer, wherein each of the three or more bodies includes at least one aperture formed therein. The three or more bodies may be daisy-chained together or may be grouped together in a specific pattern. The connection between the three or more bodies may be accomplished by connection points formed on the bodies or by utilizing a linking connector configured to link together two or more microwave spacers.

A method for placing a plurality of microwave energy delivery devices 10 and ablating tissue includes the steps of: selecting an ablation pattern; providing a pivotable microwave spacer 300; adjusting the angular relationship between the first body 311 and second body 312 of the pivotable microwave spacer 300; placing the pivotable microwave spacer 300 on a portion of patient tissue 160 adjacent a target tissue 160a; inserting two or more microwave energy delivery devices 10 through apertures formed in the first body 311 and/or the second body 312 of the pivotable microwave spacer 300 and into the target tissue 160a; connecting the microwave energy delivery devices 10 to a microwave energy source (not explicitly shown), and ablating the target tissue 160a by delivering microwave energy through the microwave energy delivery devices 10.

The method may further include the step of cooling patient tissue 160 by providing airflow between the pivotable microwave spacer 300 and patient tissue 160.

The methods may further include the step of inserting one or more sensors 315 through an available aperture (e.g., apertures 302, 304, 306 formed in the pivotable microwave spacer 300) and into the target tissue 160a. The sensor 315 may measure one or more properties of the target tissue 160a such as, for example, temperature (i.e., thermocouple, RTD or inferred heat measuring device), impedance and/or a tissue fluid content.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A spacer configured to position energy delivery devices comprising:
    a first body defining a first aperture therethrough configured for receipt of a first energy delivery device; and
    a second body pivotally coupled to the first body and defining a second aperture therethrough configured for receipt of a second energy delivery device;
    wherein the first and second bodies are configured to be moved relative to each other between a minimum angular relationship and a maximum angular relationship.

2. The spacer according to claim 1, wherein the first and second bodies cooperatively define a third aperture through the first and second bodies, the third aperture configured for receipt of a third energy delivery device.

3. The spacer according to claim 2, wherein the first, second, and third apertures form corners of an equilateral triangle when the first and second bodies are moved to one of the minimum angular relationship or the maximum angular relationship.

4. The spacer according to claim 1, wherein the first body includes:
    an upper first body member;
    a lower first body member; and
    a first body spacer interconnecting the upper and lower first body members, and
    wherein the second body includes a second body member pivotally attached to the first body between the upper and lower first body members.

5. The spacer according to claim 4, wherein the upper and lower first body members of the first body and the second body member cooperatively define a third aperture through the first and second bodies, the third aperture configured for receipt of a third energy delivery device.

6. The spacer according to claim 4, wherein the second body further includes a second body stop attached to the second body member of the second body, the second body stop configured to limit movement of the first and second bodies between an angular relationship of 30° and 330°.

7. The spacer according to claim 6, wherein the second body stop of the second body is configured to contact the upper first body member of the first body when the first and second bodies are moved to the minimum or maximum angular relationship.

8. The spacer according to claim 1, further comprising an angular gauge disposed on the first and second bodies and configured to indicate an angular measurement of an angular relationship between the first and second bodies.

9. The spacer according to claim 8, wherein the angular gauge includes:
    a first angular indicator disposed on the first body and configured to indicate the angular measurement when the angular relationship is between the minimum angular relationship and 180°; and
    a second angular indicator disposed on the second body and configured to indicate the angular measurement when the angular relationship is between 180° and the maximum angular relationship.

10. The spacer according to claim 1, further comprising a locking mechanism disposed on at least one of the first or second bodies to selectively lock the positions of the first and second bodies relative to one another.

11. The spacer according to claim 10, wherein the locking mechanism includes:
    a catch disposed on the first body; and
    a ratchet disposed on the second body and configured to engage with the catch to permit rotation of the second body relative to the first body in a first direction and to resist rotation of the second body relative to the first body in a second direction, opposite the first direction.

12. The spacer according to claim 10, wherein the locking mechanism includes:
    a protuberance extending from the first body; and
    a plurality of recessed channels formed in the second body in a circular configuration, wherein the protuberance sequentially engages each successive recessed channel of the plurality of recessed channels as the first and second bodies are moved relative to each other.

13. The spacer according to claim 1, further comprising a plurality of legs extending from the first and second bodies and configured to elevate the spacer from patient tissue.

14. An electrosurgical ablation system, comprising:
    a microwave energy source;
    a first microwave energy delivery device, a second microwave energy delivery device, and a third microwave energy delivery device each including a microwave antenna configured to radiate microwave energy received from the microwave energy source; and
    a spacer including:
        a first body defining a first aperture therethrough configured for receipt of the first microwave energy delivery device; and
        a second body pivotally coupled to the first body and defining a second aperture therethrough configured for receipt of the second microwave energy delivery device, the first and second bodies cooperatively defining a third aperture through the first and second bodies, the third aperture configured for receipt of the third microwave energy delivery device;
        wherein an angular relationship between the first and second bodies is configured to be adjusted between a minimum angular relationship and a maximum angular relationship to adjust a spatial relationship between the first and second microwave energy delivery devices.

15. The system according to claim 14, wherein the first, second, and third apertures form corners of an equilateral triangle when the first and second bodies are disposed at one of the minimum angular relationship or the maximum angular relationship.

16. The system according to claim 14, wherein the first body includes:
- an upper first body member;
- a lower first body member; and
- a first body spacer interconnecting the upper and lower first body members, and
- wherein the second body includes a second body member pivotally attached to the first body between the upper and lower first body members.

17. The system according to claim 16, wherein the second body further includes a second body stop attached to the second body member, the second body stop configured to limit the angular relationship between the first and second bodies to between 30° and 330°.

18. The system according to claim 17, wherein the second body stop of the second body is configured to contact the upper first body member of the first body when the first and second bodies are disposed at one of the minimum angular relationship or the maximum angular relationship.

\* \* \* \* \*